United States Patent
O'Neil

(10) Patent No.: US 9,820,752 B2
(45) Date of Patent: Nov. 21, 2017

(54) RELEASABLY LOCKING TIE

(71) Applicant: Terence O'Neil, Corona Del Mar, CA (US)

(72) Inventor: Terence O'Neil, Corona Del Mar, CA (US)

(*) Notice: Subject to any disclaimer, the term of this patent is extended or adjusted under 35 U.S.C. 154(b) by 167 days.

(21) Appl. No.: 14/522,356

(22) Filed: Oct. 23, 2014

(65) Prior Publication Data

US 2016/0113660 A1    Apr. 28, 2016

(51) Int. Cl.
*B65D 63/00* (2006.01)
*A61B 17/132* (2006.01)
*B65D 63/10* (2006.01)

(52) U.S. Cl.
CPC ...... *A61B 17/1322* (2013.01); *B65D 63/1063* (2013.01)

(58) Field of Classification Search
CPC .............. A61B 17/1322; B65D 63/1063
See application file for complete search history.

(56) References Cited

U.S. PATENT DOCUMENTS

| | | | | |
|---|---|---|---|---|
| 4,191,334 A * | 3/1980 | Bulanda | ................. | F16L 3/233 24/16 PB |
| RE31,689 E * | 10/1984 | Bulanda | ............. | B65D 63/1063 24/16 PB |
| 4,510,650 A * | 4/1985 | Espinoza | ................. | F16L 3/233 24/16 PB |
| 5,269,803 A * | 12/1993 | Geary | ................. | A61B 17/1322 606/201 |
| 8,499,419 B2 * | 8/2013 | Cheng | ................. | B65D 63/1063 24/16 PB |
| 8,955,198 B2 * | 2/2015 | Carnevali | .......... | B65D 63/1063 24/16 PB |
| 2004/0154139 A1 * | 8/2004 | Crook | ................. | B65D 63/1018 24/16 PB |
| 2006/0260103 A1 * | 11/2006 | Holtsch | ................. | A44B 11/06 24/136 R |
| 2016/0001945 A1 * | 1/2016 | Foreman | ................. | F16L 3/222 29/525.03 |

* cited by examiner

*Primary Examiner* — Robert J Sandy
*Assistant Examiner* — Matthew Sullivan
(74) *Attorney, Agent, or Firm* — Fulwider Patton LLP

(57) ABSTRACT

The present invention is an apparatus for releasably constricting one or more objects, and in particular to a restricting blood to an injured appendage comprising an elongate band and capture device that cooperate to form a releasable, adjustable loop. A release lever and a parallel thumb mount are compressed to release the elongate band from the capture device, where the thumb mount is configured to remain fixed while the release lever rotates about a fulcrum bar to disengage a projection that locks the size of the loop.

2 Claims, 4 Drawing Sheets

RELEASABLY LOCKING TIE

BACKGROUND OF THE INVENTION

This invention relates in general to the field of plastic ties, used generally to temporarily bind a plurality of objects, and is especially suited for blood flow restriction (e.g., a tourniquet), in an appendage such as an arm, leg, finger, or toe, quickly and reliably using a simple device that constricts and releases the appendage as required. The release feature of the present invention makes it suitable for more general purposes, and the invention is not limited to any particular use or field.

Tourniquets are well known for the purpose of temporarily restricting the flow of blood to a person's injured limb in order to prevent a serious loss of blood. In battle environments, many deaths are attributed to blood loss from extremities as a result of body armor that is applied around the trunk. Death can occur within minutes due to blood loss, so the time needed to apply a tourniquet is critical. Further, it is most advantageous if a tourniquet can be applied by the victim, but self application of a tourniquet has been at best problematic in the past. Most emergency medical technicians and paramedics have belts or cords that can be fashioned into a tourniquet when needed. However, these devices suffer from one drawback or another in that they either require the use of both hands to secure and tighten, or they are difficult to thread about the injured appendage. Further, where the injury occurs in the home or workplace and unskilled persons or the injured party themselves may be required to apply the tourniquet, previous devices and methods do not lend themselves to easy application and secure blood flow restriction. Another disadvantage is that traditional blood flow restriction devices are too large to effectively work on smaller appendages, such as fingers. However, fingers and toes suffer a disproportionately high number of cuts and lacerations, and the loss of blood from these wounds can lead to serious health consequences.

Presently, a rubber band, Penrose drain, or the finger of a rubber glove is typically used with a clamp to restrict blood flow to and through a finger. The hazard with these solutions is that they tend to roll up as they are stretched, transmitting a high force over a very small area. This concentrated force increases the risk of neurovascular damage. Furthermore, these tourniquets do not allow the amount of pressure being applied for controlling bleeding to be easily modified. As a result, they tend to be applied too tightly, causing undue force on the digit and increasing the risk of neurovascular injury.

SUMMARY OF THE INVENTION

The device used in the present invention is light-weight, sterile, disposable, reliable, and cost effective plastic tie that can be quickly locked and released. While the invention is suitable for many purposes, including those ordinarily associated with Zip Ties, the invention is also well suited for medical applications and can be kept in a first aid kit, a glove box, or purse, for emergency situations. It can also be easily and quickly applied by the victim in a reliable manner. An important feature of the present invention is that the wounded appendage does not have to be moved to apply the device, since it can be slid under the appendage and secured without the need to either lift the appendance or otherwise move it. This feature can be critical if the victim is trapped in a situation where either the victim is immobile or cannot be easily accessed, as is the case in automobile accidents and accidents involving machinery. The present method can also be used in medical procedures and surgeries where the restriction of a blood flow is needed, and can replace more expensive apparatus that performs the same function.

The present invention is small lightweight plastic tie that can be used to bind objects or as a tourniquet to restrict blood flow in an injured appendage, and can also be used to apply direct pressure to a wound when direct pressure cannot otherwise be applied to the area. This is done by placing gauze on the wound and then gently applying direct pressure with the device.

Blood flow constricting devices should not ordinarily be left in place for over one hour, as they may cause neurovascular damage. The present invention allows the tourniquet to be released for a time period, and then retightened, mitigating prolonged ischemia risks. Since the device is releasable, the pressure can be titrated and readjusted to provide only the minimum amount of pressure needed. The re-adjustable nature of the device is particularly useful for medical procedures, such as finger lacerations and ingrown toe nails, as these are particularly high vascular areas. The current standard of care is to inject a local anesthetic without epinephrine, as epinephrine has been found to cause tissue necrosis in part of the body. The addition of epinephrine would normally decrease blood flow to an area decreasing the need for a tourniquet, as the area where one would be working could more easily be visualized. However, as epinephrine cannot be used with the local anesthetic, a tourniquet is often needed to decrease bleeding in order to visualize a particular area. A tourniquet needs to be applied to digits (fingers and toes) due to their highly vascular nature.

The present invention allows for an easy, low cost way to apply the minimal amount of pressure in order to achieve vascular control. The amount of pressure can be increased or decreased easily and more accurately than previous methods using the releasable locking mechanism. In addition, the rigid nature of the apparatus prevents it from rolling up and narrowing the area of applied force, mitigating any potential neurovascular compromise. The present invention is well suited for medical procedures where a tourniquet is required, such as surgeries on the hand, arm, foot, ankle, knee, or other extremities. Once again, the pressure can easily be titrated to obtain the minimal amount of pressure needed. Additionally, it facilitates procedures outside of an operating room as expensive equipment is not needed to obtain vascular control.

One feature of the present invention is a new release mechanism for the zip tie that includes an inclined lever for engaging the zip tie free end and an inclined thumb mount extending generally parallel to the lever. The thumb mount is spaced from the lever by a gap that allows the lever to be squeezed toward the thumb mount, releasing the zip tie free end. The thumb mount is preferably thicker and has a larger base, such that when the lever and the thumb mount are squeezed together the lever moves toward the thumb mount while the thumb mount is largely fixed. This allows the release mechanism to be grasped between a thumb and forefinger and squeezed, and the lever will withdraw from the engagement with the toothed free end of the zip tie. The angle of the inclined thumb mount enables a more efficient engagement of the lever with the zip tie, since its release is made easier by the presence of the thumb mount. Both the thumb mount and the lever are preferably provided with ridges or grooves to enhance the traction and improve the grip, which can be important when there is blood, sweat, or the presence of other substances which may make the zip tie slippery or difficult to operate.

Other features and advantages of the invention will become apparent from the following detailed description, taken in conjunction with the accompanying drawings which illustrate, by way of example, the features of the invention.

DETAILED DESCRIPTION OF THE PREFERRED EMBODIMENTS

Figure 1:
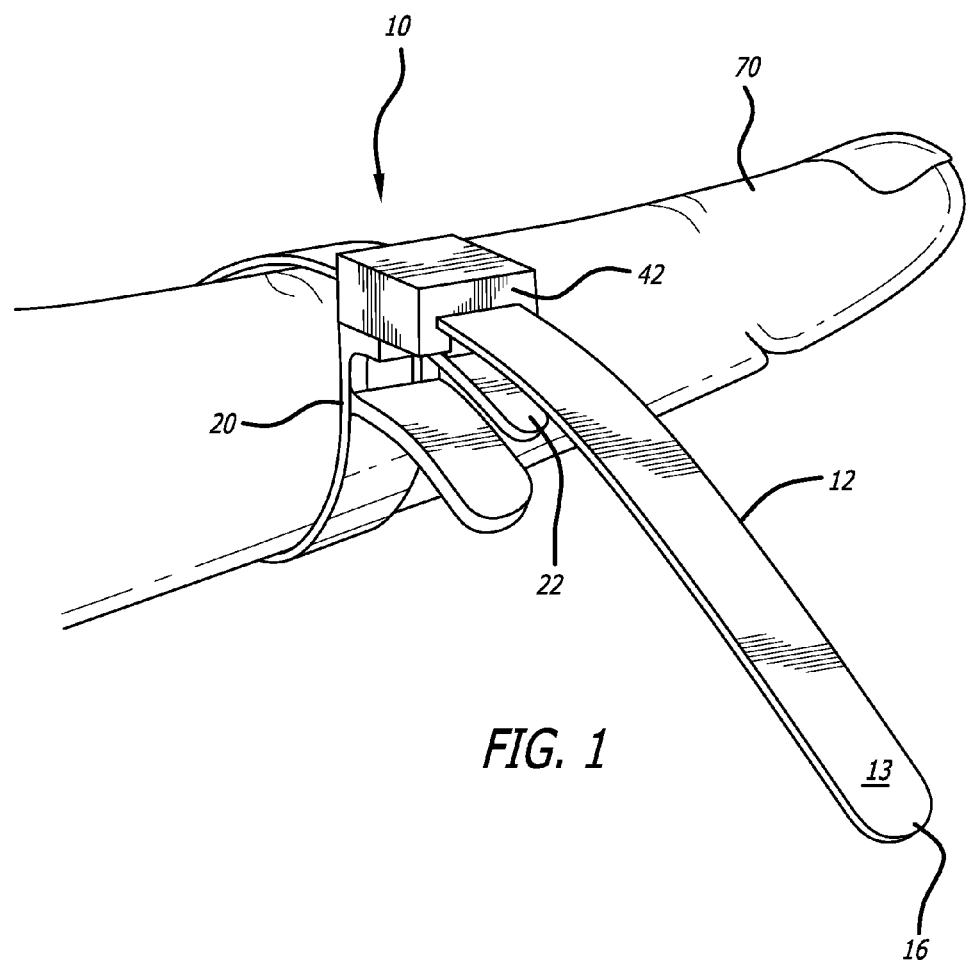
FIG. 1 is a plan view of the present invention used as a blood flow constricting device.
Figure 2:
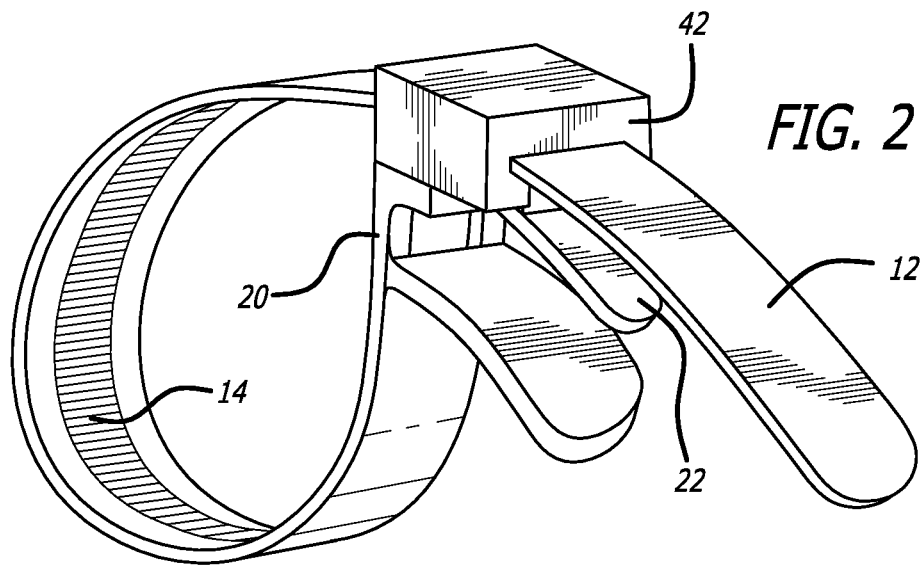
FIG. 2 is an enlarged, side perspective view of the device of FIG. 1.
Figure 3:
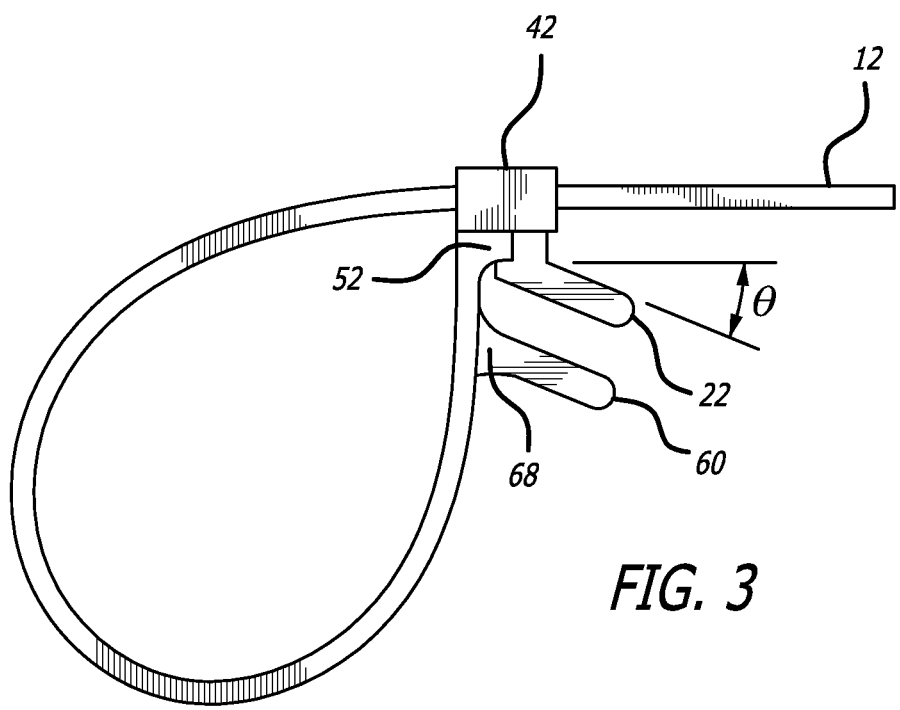
FIG. 3 is a side view of the device of FIG. 1.

For a better understanding of the present invention together with other and further objects, advantages and capabilities thereof, reference is made to the following disclosure and appended claims in connection with the above described drawings. FIG. 1 illustrates a releasable cable tie 10 of the present invention which operates in a manner such as certain cable ties offered for construction applications like those offered by KAI SUH SUH Enterprise Co., Ltd., as shown at http://www.allproducts.com/ee/kss/cable_tie.html. The cable tie 10 may be made from Nylon or plastic which has sufficient rigidity to prevent the tie from folding or rolling as pressure is applied, although any suitable material can achieve the objectives of the present invention. The cable tie 10 may be a single use application where the tie is sterile and enclosed in a sealed package until its ready for use, although in non-medical applications (see FIG. 6) the tie can be reusable and non-sterile.

Figure 4:
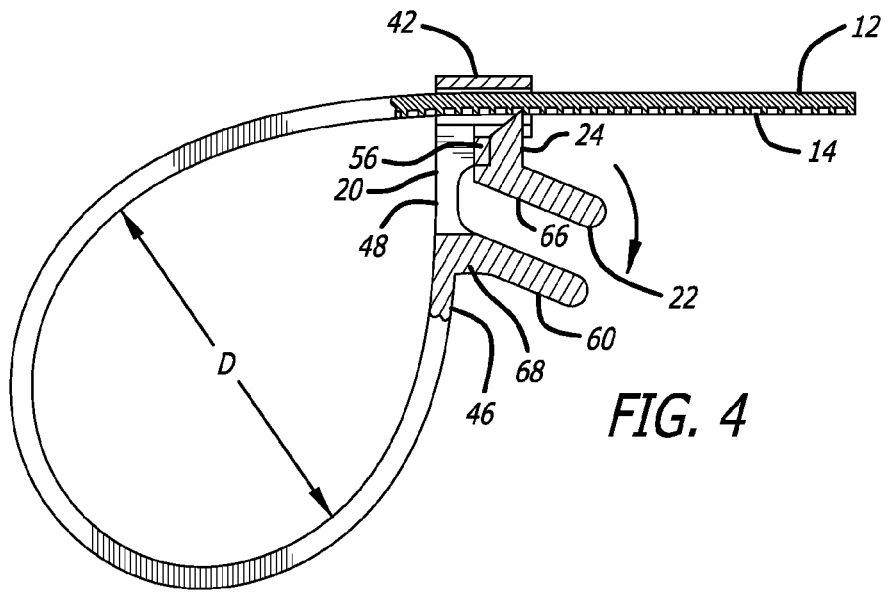
FIGS. 4 and 5 are cross-sectional views of the device of FIG. 1.
Figure 5:
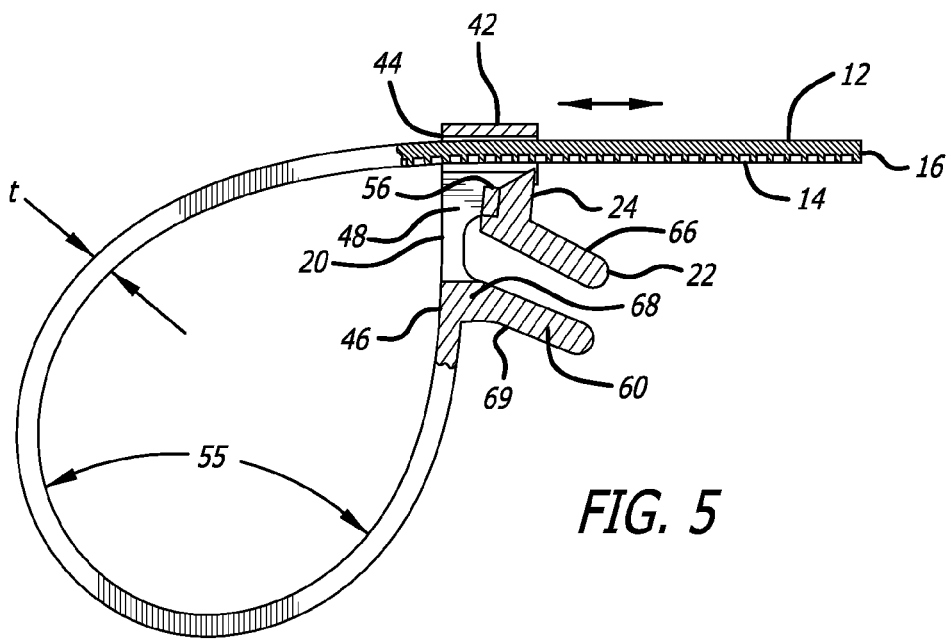

The cable tie 10 includes a free end 12 in the form of an elongate band that preferably includes a flat, smooth surface 13 on one side and closely spaced, traverse ridges/grooves 14 on the opposite side extending laterally across the band 12 in regular intervals. The distal end 16 of the tie 10 may have a rounded tip to facilitate insertion through the capture mechanism at the proximal end 20 of the tie 10. As the distal end 16 of the free end 12 is fed into and through the capture mechanism, the grooves 14 are sequentially engaged by a lever arm 22 at the capture mechanism. The lever arm 22 includes an edge-like tab or projection 24 (see FIGS. 4 and 5), that is preferably wedge shaped, and mates with each groove 14 as the free end 12 passes through the capture mechanism, preventing the free end 12 from being withdrawn back through the capture mechanism. In a preferred embodiment, the wedge-shaped projection 24 is angled like a barb, having an upper surface that forms an acute angle with the free end 12, strengthening the engagement of the projection 24 with the grooves 14. This ensures that once the free end 12 is pulled to a particular loop size D, the loop will not release as long as the lever arm 22 is not disengaged from the occupied groove. The grooves 14 on the free end 12 can alternately be replaced by projecting teeth and the lever arm 22 can be adapted with a slot or groove to receive one or more teeth to lock the lever arm in place and fix the free end 12.

The capture mechanism includes a C-shaped block 42 where the opening 44 is sized to receive the free end 12 of the tie 10. A thickness T of the C-shaped block 42 is greater than a thickness t of the free end 12 of the tie 10 to provide a sturdy and aligned entrance for the free end 12. The C-shaped block 42 is connected to the proximal end 46 of the free end 12 by left and right supports 48 extending from the proximal end 46. The supports 48 comprise longitudinal components 50 and transverse extensions 52, where the transverse extensions 52 mate with the ends 57 of the C-shaped block 42 to define a T-shaped opening 44. The free end 12 of the tie 10 is inserted into the opening 44 along the upper portion, which is sized to snugly receive the free end 12 therethrough.

The longitudinal components 50 of the supports 48 are connected together by a fulcrum bar 56 at the connection of the C-shaped block with the supports 48. The fulcrum bar 56 mounts a locking mechanism comprising the lever arm 22 and an integral wedge-shaped projection 24 pointing inwardly at the exit of the C-shaped block 42. The lever arm 22 includes an release extension 66 that is oriented at an angle θ that is approximately thirty degrees (30°) in an unbiased position with respect to a plane defining the ingress and egress of the free end 12 through the upper portion of the opening 54 of the C-shaped block 42. An downward force (See FIGS. 4, 5) applied to the lever arm 22 at the release extension 66 rotates the lever arm 22 and the wedge-shaped projection 24 about the fulcrum bar 56, causing disengagement of the wedge-shaped projection 24 from the grooves 14 on the surface of the free end 12. In this manner, the loop 55 formed by the free end as it is captured by the capture mechanism can be adjusted by positioning the wedge-shaped projection 24 of the lever arm 22 into the correct groove to apply the correct amount of pressure.

To aid in applying the upward force on the lever arm 22, a thumb mount 60 is formed on the proximal end 46 of the free end 12. The thumb mount 60 comprises a thumb plate 62 having a width that is substantially the width of the free end 12, and may include frictional ridges on a lower surface 69 to improve the gripping characteristics of the thumb mount 60. The thumb mount 60 is cantilevered to the proximal end 46 of the free end 12 at an angle that orients the thumb mount 60 and the lever arm 22 approximately parallel, i.e., about thirty degrees (30°) from the exit plane of the free end 12 emerging from the capture device. The thumb mount 60 is connected to the free end 12 using a reinforced attachment 68, whereby a thickness of the intersection of the thumb plate 62 with the free end 12 is approximately twice the thickness of the thumb plate 62. This added reinforcement ensures that the thumb plate remains essentially fixed while a compressive force is applied to the thumb mount 60 and lever arm 22, such that the lever arm 22 moves toward the thumb mount 60 and not vice-versa. This ensures that the wedge-shaped projection 24 will disengage with the grooves 14 on the free end when the thumb mount and lever are squeezed together.

In operation, when the tie 10 is needed to restrict blood flow in an appendage such as a finger 70, the tie is preferably removed from a sterile packaging and brought in proximity with the patient. With the grooved surface facing upward, the free end 12 of the tie 10 is bent backwards and inserted into the upper portion of the T-shaped opening 44 in the C-shaped block 42 to form a loop 55. The loop 55 is then placed over the appendage 70 between the wound/surgical location and the victim's heart so as to be in position to restrict blood flow to the area. The free end 12 of the tie 10 is pulled slowly through the capture mechanism, until the wedge shaped projection 24 of the lever arm 22 engages the first groove 14 on the surface of the free end 12. As the free end 12 is pulled farther through the opening 44, each successive groove 14 is engaged by the wedge-shaped projection 24, such that it withdrawal of the free end 12 is prevented by such engagement. This process establishes the size of the loop 55 and accompanying pressure thereby applied to the finger 70. The tie 10 is tightened around the appendage 50 until the requisite amount of pressure is applied to restrict the flow of blood to the designated area, whereupon the pulling of the tie is ceased.

If the flow of blood requires adjusting, the flow can be restricted further by simple pulling the tie 10 one groove 14 at a time until the correct pressure is achieved. If the pressure needs to be lessened, or the device removed, the user places a thumb on the thumb mount 60 and a finger on the lever arm 22, and applies a compressive force to squeeze the two extensions together. Due to the reinforced thickness 68 at the thumb mount's connection to the free end 12, the compression will move the lever arm 22 toward the thumb mount 60 and away from the free end 12. This movement releases the wedge-shaped projection 24 from its occupied groove 14, allowing the free end 12 to be withdrawn from the capture mechanism. This process can be repeated as necessary to gradually tighten or loosen the pressure applied by the tie device 10.

Figure 6:
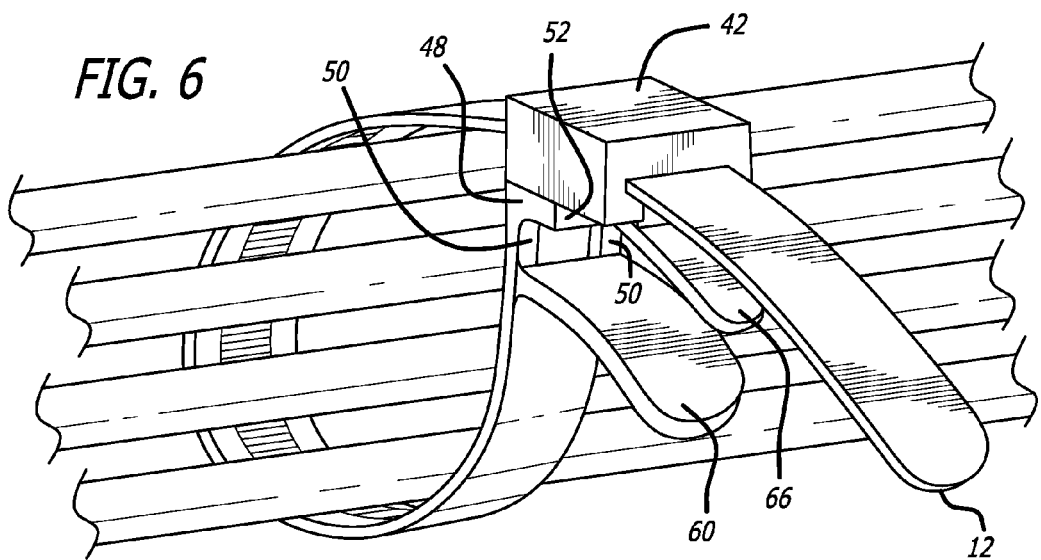
FIG. 6 is an elevated perspective view of the invention used in a non-medical application.
Figure 7:
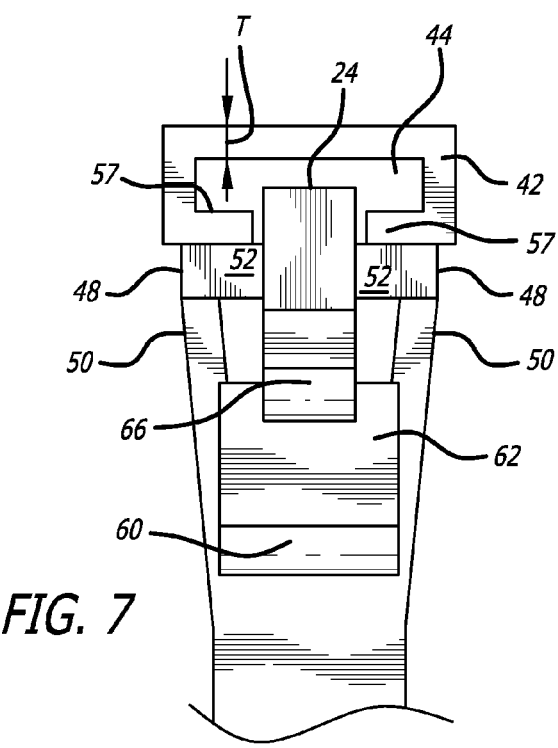
FIG. 7 is a front view of the thumb mount and release lever.

FIG. 6 illustrates alternative uses for the invention 10, including binding and gathering various objects, especially elongate objects. The invention is thus not limited to any particular usage, but rather is and should be considered a general purpose tie.

The method and apparatus just described is illustrative of the present invention, and should not be deemed to be limiting in any manner. Rather, the scope of the invention is properly considered to include all variations and modifications that would be considered by those of ordinary skill in the art. Accordingly, the invention is properly measured not by the aforementioned description but rather by the words of the appended claims and all equivalents attributable thereto.

I claim:

1. A releasable plastic tie having a capture mechanism connected to an elongate band at a proximal end for locking a distal end of the releasable plastic tie, comprising:

a plurality of alternating ridges and grooves extending traversely along a length of the elongate band on a first surface; and the capture mechanism including:

first and second supports extending longitudinally from a proximal end of the elongate band;

a C-shaped block connected to the first and second supports, where the C-shaped block and the first and second supports define a T-shaped opening;

a fulcrum bar connecting the first and second supports at the C-shaped block, the fulcrum bar cooperating with the C-shaped block to define a pathway for a free end of the elongate band;

a lever arm connected to the fulcrum bar for pivoting movement thereabout, the lever arm including a release extension projecting at an acute angle with a plane defined by the free end of the elongate band as it exits the C-shaped block, and an engagement projection downwardly extending toward the elongate band and adapted to engage successive ridges on the elongate band to fix the elongate band within the C-shaped block, and a thumb mount extending from the elongate band and spaced from the release extension of the lever arm in a substantially parallel relationship with the lever arm, the thumb mount connected to the elongate band to resist movement of the thumb mount when a compressive force is applied to the thumb mount and the release extension of the lever arm, the thumb mount cantilevered at an angle of thirty degrees (30°) from an exit plane of the distal end of the releasable plastic tie exiting the capture mechanism, the thumb mount further comprising ridges on a first surface for improved tactile response, and the thumb mount further comprising a wedge shaped attachment to the elongate band to double a thickness of the thumb mount at the elongate band.

2. The releasable plastic tie of claim 1, wherein the engagement projection is wedge shaped.

* * * * *